US012758233B2

(12) United States Patent
Firmbach et al.

(10) Patent No.: US 12,758,233 B2
(45) Date of Patent: Oct. 13, 2026

(54) SURGICAL INSTRUMENT

(71) Applicant: Aesculap AG, Tuttlingen (DE)

(72) Inventors: Franz-Peter Firmbach, Emmingen-Liptingen (DE); Lilli Stoffels, Calw (DE)

(73) Assignee: Aesculap AG, Tuttlingen (DE)

( * ) Notice: Subject to any disclaimer, the term of this patent is extended or adjusted under 35 U.S.C. 154(b) by 466 days.

(21) Appl. No.: 18/348,015

(22) Filed: Jul. 6, 2023

(65) Prior Publication Data

US 2024/0023972 A1 Jan. 25, 2024

(30) Foreign Application Priority Data

Jul. 25, 2022 (DE) ..................... 10 2022 207 575.7

(51) Int. Cl.
*A61B 17/15* (2006.01)

(52) U.S. Cl.
CPC .................................. *A61B 17/157* (2013.01)

(58) Field of Classification Search
CPC ...................... A61B 17/155; A61B 2017/0268
See application file for complete search history.

(56) References Cited

U.S. PATENT DOCUMENTS 4,907,578 A * 3/1990 Petersen .............. A61B 17/155 606/88
5,484,446 A * 1/1996 Burke .................. A61B 17/154 606/86 R
5,735,904 A * 4/1998 Pappas .................. A61F 2/4684 623/908
5,749,876 A * 5/1998 Duvillier .............. A61B 17/155 606/88
6,056,756 A * 5/2000 Eng ........................ A61F 2/4657 606/88
6,468,280 B1 * 10/2002 Saenger ............... A61B 17/155 606/88
8,475,462 B2 * 7/2013 Thomas ................. A61B 17/15 606/87
9,498,199 B2 11/2016 Colquhoun et al.
10,166,034 B2 1/2019 Claypool et al.
10,682,195 B2 * 6/2020 Tredinnick ............. A61B 90/11
12,465,404 B2 * 11/2025 Smyth ................ A61B 17/6458
12,471,933 B2 * 11/2025 Prien .................. A61B 17/7241
2006/0200158 A1 * 9/2006 Farling ................ A61B 17/155 606/87

(Continued)

FOREIGN PATENT DOCUMENTS

WO 2011018647 A1 2/2011

*Primary Examiner* — David W Bates
(74) *Attorney, Agent, or Firm* — Christopher A. Rothe; CM Law

(57) ABSTRACT

A surgical instrument for use in a total knee arthroplasty includes a first fastening device and a guide device releasably coupled to the first fastening device and configured for releasable coupling to a second fastening device. The guide device has a sliding guide with at least one guide slot extending longitudinally along a guide track and at least one sliding member which is received in the at least one guide slot so as to be slidingly movable along the guide track. The first fastening device has at least one push-fit receiver, by which the at least one sliding member is introduced into the at least one guide slot forming a releasable push-fit connection with the first fastening device.

20 Claims, 7 Drawing Sheets

(56) References Cited

U.S. PATENT DOCUMENTS

| | | | | |
|---|---|---|---|---|
| 2008/0195110 | A1* | 8/2008 | Plassy | A61B 17/154 606/88 |
| 2009/0043310 | A1* | 2/2009 | Rasmussen | A61B 17/1764 606/88 |
| 2009/0222014 | A1* | 9/2009 | Bojarski | A61B 17/1615 606/88 |
| 2009/0287216 | A1* | 11/2009 | Warkentine | A61B 17/154 606/87 |
| 2010/0241126 | A1* | 9/2010 | Ghijselings | A61B 17/155 606/88 |
| 2010/0305711 | A1* | 12/2010 | McKinnon | A61B 17/157 606/82 |
| 2012/0245588 | A1* | 9/2012 | Murray | A61B 17/155 606/87 |
| 2014/0288563 | A1* | 9/2014 | Claypool | A61B 17/155 606/88 |
| 2015/0045801 | A1* | 2/2015 | Axelson, Jr. | A61B 17/15 606/88 |
| 2018/0177612 | A1* | 6/2018 | Trabish | A61B 90/06 |
| 2020/0155168 | A1* | 5/2020 | Minfelde | A61F 2/4684 |
| 2021/0000484 | A1* | 1/2021 | Goble | A61B 17/164 |
| 2022/0192774 | A1* | 6/2022 | Goble | A61F 2/3859 |
| 2023/0380844 | A1* | 11/2023 | Firmbach | A61B 17/1659 |
| 2024/0023971 | A1* | 1/2024 | Firmbach | A61B 17/157 |
| 2024/0023973 | A1* | 1/2024 | Firmbach | A61B 17/157 |
| 2024/0024131 | A1* | 1/2024 | Firmbach | A61F 2/3859 |

* cited by examiner

Detail A

Section B-B

Detail D

SURGICAL INSTRUMENT

CROSS-REFERENCE TO RELATED APPLICATIONS

This application claims priority under 35 U.S.C. § 119 to German Application No. 10 2022 207 575.7, filed on Jul. 25, 2022, the content of which is incorporated by reference herein in its entirety.

FIELD

The present disclosure concerns a surgical instrument for use in a total knee arthroplasty.

BACKGROUND

In a total knee arthroplasty (TKA), the joint surfaces of the femur and/or the tibia, which are worn or have otherwise been damaged by disease or accident, are replaced by artificial joint surfaces of a knee prosthesis. Such knee prostheses usually comprise a femoral component and a tibial component. The femoral component is implanted at the distal end of the femur. The tibial component is implanted at the proximal end of the tibia.

Before implantation of the prosthetic components, the distal femur and the proximal tibia are resected. For this, the surgeon makes various resection cuts and detaches bone and/or cartilage material from the respective bone. The resection adapts the shape of the respective bone to the prosthetic components to be received.

Resection may be carried out on the basis of various concepts. One concept is targeted at maintaining balanced tensions on the ligaments of the knee during joint movement. This aims to guarantee better function of the knee joint prosthesis. This concept is generally known as "gap balancing". In other concepts, the surgeon removes a certain quantity of bone and/or cartilage material by means of resection. Such concepts are generally described as "measured resection". The alignment of the resection cuts relative to the anatomy of the patient determines the later alignment of the implanted components, and accordingly also the orientation of the prosthetic joint axes. The alignment of the resection cuts is therefore particularly important.

For the alignment of the resection cuts, there are primarily three different approaches: mechanical, anatomical and kinematic. In mechanical alignment, the proximal tibia is resected perpendicularly to the longitudinal axis of the tibia shaft. Resection of the distal femur is adapted thereto accordingly. If necessary, ligament releases are carried out. With anatomical alignment, the aim is to resect the tibia at a varus angle of 3°. The femur resection and ligament releases are carried out with the aim of a straight hip-knee-ankle axis of the leg. The aim of kinematic alignment (KA) is to implant the artificial joint surfaces of the prosthetic components at the level of the pre-arthritic, defect-free, natural joint surfaces.

In a KA, the resection cuts are often aligned starting from the distal femur. Resection of the proximal tibia is adapted thereto. For the purpose of the successive resection of femur and tibia, special surgical instruments are known which are also called tibial cut alignment guides. Such instruments allow the alignment of the femoral resection cuts to be transferred to the tibia. Transfer usually takes place following an at least distal resection of the femur in which the distal condyles are separated. Transfer can take place in extension or flexion. In a variant of the KA, firstly the distal femur is fully prepared (all femur first). The resection cuts to be made at the distal femur are aligned to the patient's anatomy and made on the distal femur. Then a femoral trial condyle implant is arranged on the distal femur. The femoral trial condyle implant, already aligned to the patient's anatomy, is then used as a reference component, the alignment of which is transferred to the proximal tibia by means of the surgical instrument or alignment guide in order to align and produce the resection cuts to be made thereon. It is evident that alternatively, a procedure in reverse order is conceivable, i.e. starting from the proximal tibia.

Surgical instruments for a KA usually have a first fastening device which is configured for releasable fastening to a femoral or tibial reference component. Typically, a guide device is provided on which a tibial or femoral cutting block can be fastened. This means that such a surgical instrument can be used in principle either together with a femoral reference component and a tibial cutting block, or alternatively together with a tibial reference component and a femoral cutting block. The guide device allows a guided relative movement between the reference component and the cutting block.

Before re-use, the surgical instrument must usually be cleaned, in particular sterilised. In particular in the region of the guide device, there are often locations with difficult access which cannot be reached, or only reached with difficulty, for cleaning without separating the guide device from the other components of the surgical instrument. In this connection, it is desirable if the surgical instrument can be at least partially dismantled into its component parts.

SUMMARY

The object of the present disclosure is to provide a surgical instrument which offers advantages over conventional surgical instruments, and in particular can be at least partially dismantled into its component parts without a separate mounting tool.

The surgical instrument according to the present disclosure serves for use in a total knee arthroplasty and comprises: a first fastening device which is configured for releasable fastening to a femoral reference component, a guide device which is firstly releasably coupled to the first fastening device and secondly can be coupled to a second fastening device which is configured for releasable fastening to a tibial component, and allows a relative movement guided in a sagittal guide plane between the first fastening device and the second fastening device, wherein the guide device comprises a sliding guide with at least one guide slot longitudinally extending along a guide track and at least one sliding member which is received in the at least one guide slot so as to be slidingly movable along the guide track, and wherein the first fastening device has at least one push-fit receiver which extends orthogonally to the guide track and via which the at least one sliding member is introduced into the at least one guide slot, forming a releasable push-fit connection with the first fastening device. Alternatively or additionally, the first fastening device may be configured for releasable fastening to a tibial reference component. Alternatively or additionally, the second fastening device may be configured for releasable fastening to a femoral component. The surgical instrument can thus be used in a KA starting from the tibia and/or in a KA starting from the femur. Neither the femoral reference component nor the tibial component nor the second fastening device are part of the surgical instrument. The guide track is preferably arranged in or parallel to the guide plane. The at least one sliding member serves for coupling the first fastening device to the guide device. Advantageously, the at least one sliding member thus fulfils two functions simultaneously. Firstly, it allows the slidingly movable connection of the first fastening device to the guide device. Secondly, it also allows a particularly simple dismantling of the surgical instrument into its component parts, in that it is removed from the at least one guide slot by release of the push-fit connection. Suitably, the push-fit connection can be released and/or created manually, in particular without tools. Thus, the surgical instrument can be cleaned particularly easily and thoroughly. Also, if necessary, the surgical instrument can easily be manually dismantled or reassembled during the total knee arthroplasty. Accordingly, the first fastening device may be separately fastened to the reference component, which is already mounted on the respective bone, before the guide device is mounted on the first fastening device by means of the push-fit connection. This gives advantages in the handling of the surgical instrument.

The positional and directional designations used in this description refer to a patient's body, in particular the femur, and to this extent should be understood in their normal anatomical meaning. Consequently, "anterior" means front or at the front, "posterior" means rear or at the rear, "medial" means inner or on the inside, "lateral" means outer or on the outside, "proximal" means towards the body centre and "distal" means away from the body centre. Furthermore, "proximodistal" means along, preferably parallel to a proximal-distal axis; "anteroposterior" means along, preferably parallel to an anterior-posterior axis; and "mediolateral" means along, preferably parallel to a medial-lateral axis. Said axes are oriented orthogonally to one another and may evidently be set in relation to X, Y and Z axes which are not connected to the patient's anatomy. For example, the proximal-distal axis may alternatively be designated the X axis. The medial-lateral axis may be designated the Y axis. The anterior-posterior axis may be designated the Z axis. For greater clarity and for simplicity of the designations, said anatomical positional and directional designations are primarily used below.

In one embodiment, the at least one sliding member has a sliding portion and a push-fit portion, wherein for slidingly movable guidance along the guide track, the sliding portion engages in the at least one guide slot and the push-fit portion is releasably received in an associated receiving opening of the push-fit receiver. Preferably, between its sliding portion and its push-fit portion, the at least one sliding member extends transversely to the guide track. Preferably, the push-fit portion is tightly received in the associated receiving opening by form fit and/or force fit. Preferably, the sliding portion is received in the at least one guide slot in the manner of a, in particular tight, clearance fit. Thus, a particularly precise, low-tolerance but nonetheless releasable, relatively movable connection can be achieved between the first fastening device and the guide device. Accordingly, the alignment of a resection cut can be transferred particularly precisely by means of the surgical instrument.

In a further embodiment, two sliding members are present and spaced apart from one another, in particular along the guide track. This allows a particularly reliable guidance. In particular, tilting of the sliding members in the at least one guide slot is countered. Also, the resulting push-fit connection can be loaded comparatively more greatly.

In a further embodiment, a carrier element is present on which the at least one sliding member is fastened. Preferably, the sliding member is fastened to the carrier element by substance bonding and/or by friction fit and/or form fit. By means of the carrier element, in a particularly simple fashion, the at least one sliding member can be introduced into the push-fit receiver and guide slot so as to form the push-fit connection, and conversely removed, in particular extracted, from the push-fit receiver and guide slot. In other words, the carrier element improves the handling of the sliding member for mounting or removal.

In a further embodiment, the carrier element has a base body and a handle portion protruding from the base body, in particular orthogonally to the guide track. The handle portion is preferably formed as a half ring. By means of the handle portion, the carrier element and the at least one sliding member attached thereto can be manually mounted or removed particularly easily. No separate tool is required for this. Even if the sliding member and/or the carrier element are slippery due to the presence of fluid or the like, the handle portion can be gripped securely without slipping. Furthermore, the sliding member can be easily removed even if movement is difficult because of contamination.

In a further embodiment, the sliding guide, in particular the at least one guide slot, comprises a hole row with several holes extending axially transversely to the guide track for latching of the at least one sliding member, wherein the holes are spaced apart from one another along the guide track and establish several latching positions for the at least one sliding member. The distance present between the holes here preferably relates to extent axes of the holes. The holes may be configured as bores. The centre longitudinal axes of the bores may correspond to their extent axes. The holes or bores may touch or intersect one another radially. In particular, virtual or actual circumferential geometries of the holes or bores may touch or intersect radially. Thus, advantageously, a further function may be integrated in the at least one sliding member. In this embodiment, in addition to guidance and releasable fastening, it also serves for fixing a movability of the guide device in a momentary latching position.

In a further embodiment, the at least one guide slot and/or the at least one sliding member is spring-elastically deformable against a return force, wherein the at least one sliding member is held in its momentary latching position by means of the return force. A material delimiting the at least one guide slot, and/or a material of the at least one sliding member, may for this be designed to be spring-elastically deformable. Accordingly, when the return force of a load is built up, the material may yield reversibly to a sufficient extent. After the load is removed, the original geometry is resumed as the return force diminishes. In one embodiment, the spring-elastically deformable guide slot can be widened spring-elastically. In one embodiment, the spring-elastically deformable sliding member can be compressed spring-elastically. Accordingly, the at least one sliding member automatically latches in its momentary latching position. Accordingly, the surgical instrument may be used particularly intuitively.

In a further embodiment, a fixing device is provided which is switchable between a fixing state for fixing, in particular by form fit and/or force fit, the first fastening device relative to the guide device, and a release state in which the fixing is cancelled, in particular released. Preferably, in the fixing state, the movability of the guide device is fixed by means of the fixing device. Advantageously, in this way a precise performance of a resection cut aligned by means of the surgical instrument can be ensured. In particular, the fixing device may prevent the previously correct alignment being falsified by an accidental movement of the guide device relative to the first fastening device.

In a further embodiment, the fixing device comprises a tooth row extending parallel to the guide track and an engagement device which, in the release state, is adjustably movable relative to the tooth row parallel to the guide track, wherein the tooth row is fastened to the guide device and the engagement device is mounted on the first fastening device, in particular immovably in at least one direction transversely to the guide track, or vice versa. Such a fixing device has proved particularly robust.

In a further embodiment, the engagement device comprises a form-fit element which is adjustably movable transversely to the guide track between an engagement position and a release position for switching between the fixing state and the release state, wherein the form-fit element in its engagement position engages in the tooth row and in its release position, such an engagement is eliminated, in particular released. By means of such a fixing device, the movability of the guide device can be fixed particularly reliably. In particular, there is a sufficiently great resistance against accidental adjustment of the guide device.

In a further embodiment of the present disclosure, the form-fit element is configured complementary to at least a part region of the tooth row. This advantageously allows a particularly low-tolerance fixing of the movability of the guide device.

In a further embodiment, the engagement device comprises a biasing member which biases the form-fit element into the engagement position. The engagement element may thus automatically assume its engagement position if it is not deliberately held manually in its release position. Thus, accidental adjustment of the surgical instrument after a previous alignment to the reference component is countered.

In a further embodiment, the engagement device comprises a gearwheel which is mounted so as to be blockable and rotationally movable, and which meshes in the tooth row and blocks in the fixing state and is rotationally movable in the release state. Thus advantageously, the movability of the guide device can be established at least approximately steplessly. The gearwheel may be blockable by friction fit and/or form fit. For friction-fit blocking, for example an axial mounting of the gearwheel may be constricted until the gearwheel is clamped by friction fit in its axial mounting. For form-fit blocking, for example a blocking element may be provided which is radially adjustable and rotationally rigidly mounted relative to the gearwheel, and which can be brought into engagement with the toothing of the gearwheel.

In a further embodiment, the engagement device comprises an actuating element by means of which the engagement device can be actuated, in particular manually, for switching between the release state and the fixing state. Thus, the surgical instrument can be particularly intuitively adapted to an anatomy of the patient. The actuating element may comprise a mechanism which holds the engagement element in its engagement position. Such a mechanism may be based, functionally and with respect to its construction, on a mechanism known for extension and retraction of a ballpoint pen tip. Thus, the surgeon need not permanently hold the actuating element pressed when adjusting the surgical instrument. The surgeon therefore has both hands available for performing the alignment of the resection cut to be made.

In a further embodiment, the at least one sliding member is a, in particular cylindrical, pin. Such pins are cheap to produce and/or available as standard products.

In a further embodiment, the guide track extends in arcuate form within the sagittal guide plane. Advantageously, the first fastening device and the guide device are pivotably movable relative to one another. In use of the surgical instrument in this embodiment, the first fastening device is thus releasably attached to the reference component mounted on the femur or tibia. The tibial or femoral cutting block functioning as the tibial or femoral reference component is releasably fastened to the second fastening device. The reference component is preferably a femoral trial condyle implant. In this case, the surgical instrument is particularly suitable for use in the all femur first variant of the KA. The femoral or tibial cutting block may be used for cut guidance on the distal femur or on the proximal tibia or the like. The guide device allows a guided pivot movement of the second fastening device relative to the first fastening device. On use of the surgical instrument, the guide device accordingly allows a correspondingly guided relative movement of the respective cutting block relative to the respective reference component. Thus, the slope of the cutting block in the guide plane can be set. The guide plane is aligned sagittally and accordingly extends in the anteroposterior and proximodistal directions. Preferably, a pivot axis, about which the two fastening devices are pivotably guided relative to one another by means of the guide device, intersects a mechanical tibial axis in the sagittal guide plane. Said slope is also described as a posterior or anterior slope. The ability to set the slope of the cutting block firstly allows adaptation to pre-operatively established parameters. Secondly, flexion or extension of the leg may be considered and compensated by the movability of the guide device. Thus, it may be ensured that a setting of the slope does not simultaneously lead to an undesired change of a proximodistal position of the cutting block and hence a so-called cutting height.

It is understood that the above-mentioned features and those to be explained below may be used not only in the combination explicitly described but also in other combinations or alone without leaving the scope of the present disclosure.

BRIEF DESCRIPTION OF THE DRAWING FIGURES

Further advantages and features of the present disclosure follow from the following description of preferred exemplary embodiments of the present disclosure which are illustrated in the drawings.

DETAILED DESCRIPTION

Figure 2:
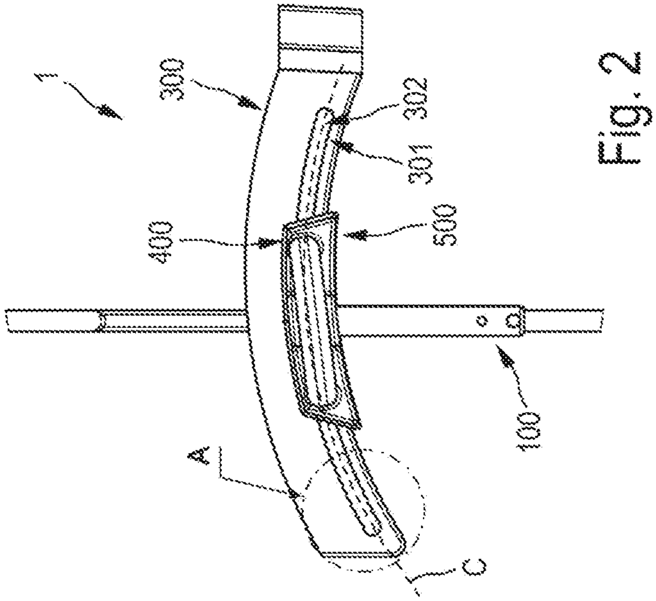
FIG. 2 shows a schematic side view of the surgical instrument from FIG. 1.
Figure 1:
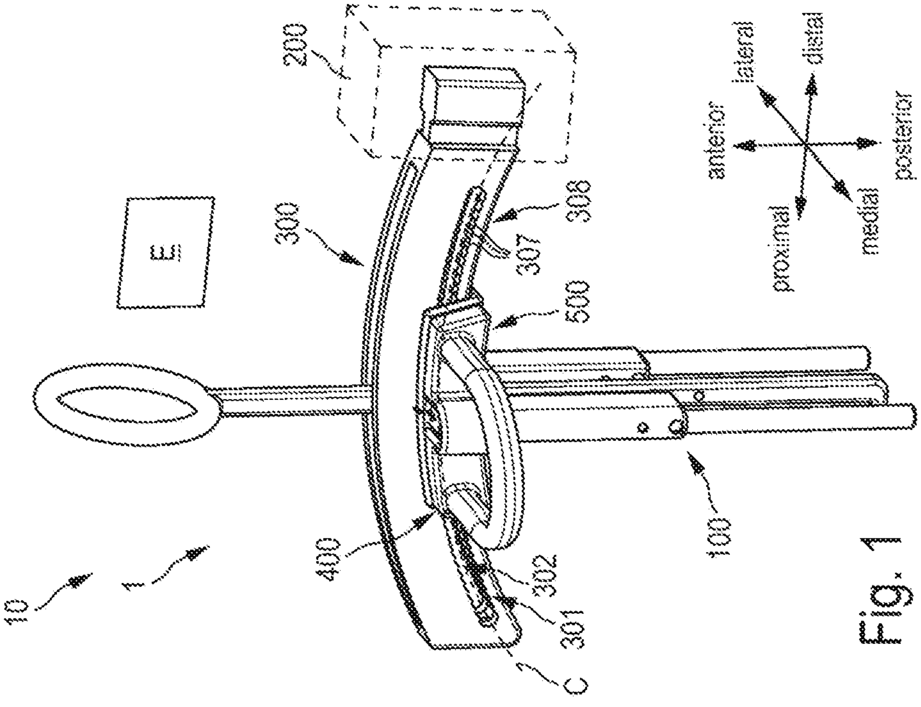
FIG. 1 shows a schematic perspective view of an embodiment of a surgical instrument according to the present disclosure.
Figure 3:
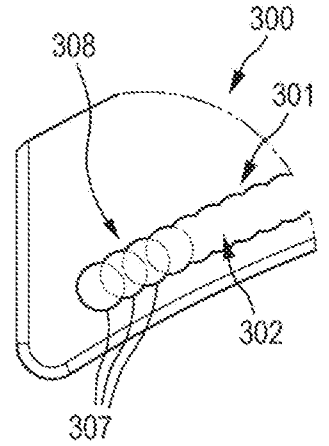
FIG. 3 shows a detail of the view in FIG. 2.
Figure 4:
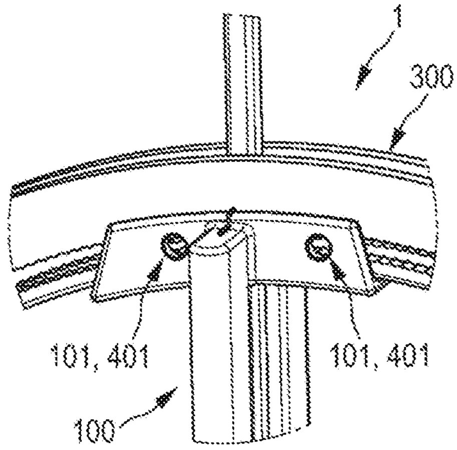
FIG. 4 shows a detail of a schematic perspective view of the surgical instrument from FIGS. 1 to 3 in partially dismantled state for greater clarity.
Figure 5:
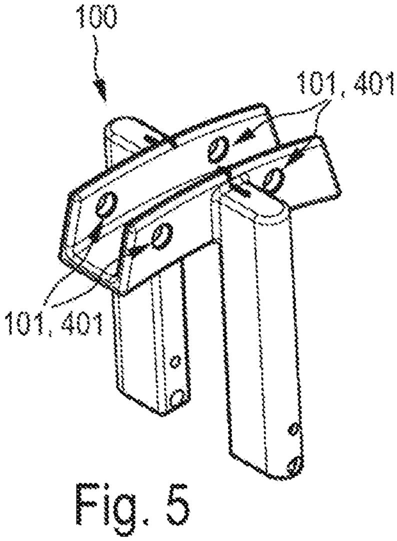
FIG. 5 shows a schematic perspective view of a first fastening device of the surgical instrument from FIGS. 1 to 4.
Figure 6:
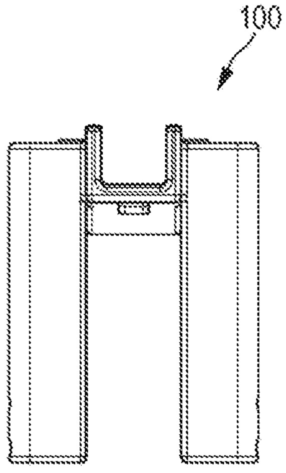
FIG. 6 shows a schematic front view of the first fastening device from FIG. 5.
Figure 7:
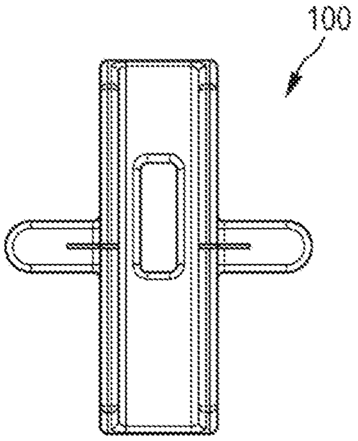
FIG. 7 shows a schematic plan view of the first fastening device from FIGS. 5 and 6.
Figure 8:
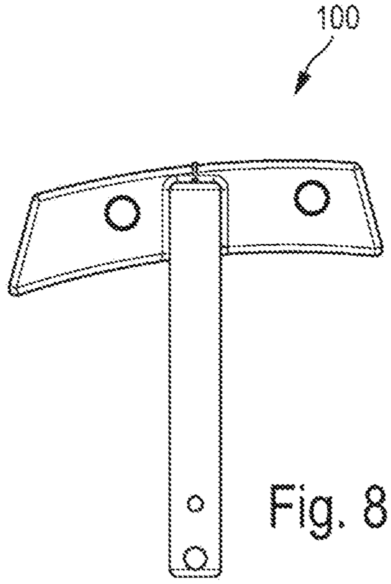
FIG. 8 shows a schematic side view of the first fastening device from FIGS. 5 to 7.

A surgical instrument 1 according to FIGS. 1 to 4 is provided for use in a total knee arthroplasty. The surgical instrument 1 may also be described as a tibial transfer tool serving for referenced positioning of a tibial cutting block (not shown in the Figures) on a proximal tibia (also not shown). A reference component (also not shown in the Figures) already positioned on a distal femur serves as a reference for the position of the tibial cutting block. The surgical instrument 1 is particularly suitable for total knee arthroplasty operations which follow the so-called all femur first approach. In this approach, first all necessary femoral resection cuts are made. After resection of the distal femur, a femoral trial condyle implant is attached to the distally resected femur, the trial condyle implant functioning as a femoral reference component for the surgical instrument 1. By means of the surgical instrument 1, an alignment of the trial condyle implant already adapted to the anatomy of the patient can be transferred to a proximal tibia in order to make at least one resection cut in the correct alignment there. As an alternative to the femoral trial condyle implant, a so-called femoral cutting block may be used as a reference component if the surgeon follows an approach other than the all femur first. The above apply similarly to the surgical instrument 1' according to FIGS. 11 to 16.

The femoral reference component is not part of the surgical instrument 1, 1'.

The surgical instrument 1, 1' comprises a first fastening device 100, 100'. The first fastening device 100, 100' is configured for releasable fastening to the femoral reference component. In principle, the first fastening device 100, 100' may, alternatively or additionally, also be configured for releasable fastening to a tibial reference component. The surgical instrument 1, 1' comprises a guide device 300, 300'. The guide device 300, 300' is releasably coupled firstly to the first fastening device 100, 100'. Secondly, the guide device 300, 300' may be coupled to a second fastening device 200, which is merely indicated as an example in FIG. 1. The guide device 300, 300' allows a guided relative movement between the first fastening device 100, 100' and the second fastening device 200 within a sagittal guide plane E. The second fastening device 200 is configured for releasable fastening to a tibial component. It is understood that the second fastening device 200 may, alternatively or additionally, in principle also be configured for releasable fastening to a femoral component. In other words, a tibial reference component is used together with a femoral component, and a femoral reference component together with a tibial component.

Neither the second fastening device 200 nor the tibial component are part of the surgical instrument 1, 1'.

The guide device 300, 300' comprises a sliding guide 301, 301'. The sliding guide 301, 301' has at least one guide slot 302, 302' longitudinally extending at least along a guide track C. The guide track C runs in or parallel to the guide plane E. The sliding guide 301, 301' furthermore comprises at least one sliding member 303, 303', **303*a*, 303*a*', 303*b*, 303*b*' which is received in the at least one guide slot 302, 302' so as to be slidingly movable along the guide track C. The first fastening device 100, 100' has at least one push-fit receiver 101, 101' extending orthogonally to the guide track C. Via this at least one push-fit receiver 101, 101', the at least one sliding member 303, 303', 303*a*, 303*a*', 303*b*, 303*b*' can be introduced into the at least one guide slot 302, 302' to form a releasable push-fit connection 400, 400' with the first fastening device 100, 100'. The push-fit connection 400, 400' serves for coupling the first fastening device 100, 100' to the guide device 300, 300'. Thus, the sliding member 303, 303', 303*a*, 303*a*', 303*b*, 303*b*' has a double function: firstly to form the releasable push-fit connection 400, 400', and secondly for guidance in the at least one guide slot 302, 302'. In the present case, the surgical instrument 1, 1' has two sliding members 303, 303', 303*a*, 303*a*', 303*b*, 303*b*'. The two sliding members 303, 303', 303*a*, 303*a*', 303*b*, 303*b*' are spaced apart from one another, for example along the guide track C. A push-fit receiver 101, 101' may be assigned to each sliding member 303, 303', 303*a*, 303*a*', 303*b*, 303*b*'**.

In the present case, the guide track C extends in arcuate form within the sagittal guide plane E. Thus, the first fastening device 100, 100' and the guide device 300, 300' are pivotably movable relative to one another within the guide plane E. If a second fastening device 200 is attached to the guide device 300, 300', the first and second fastening devices 100, 100', 200 are thus guided pivotably movably relative to one another within the guide plane E by means of the guide device 300, 300'.

Figure 10:
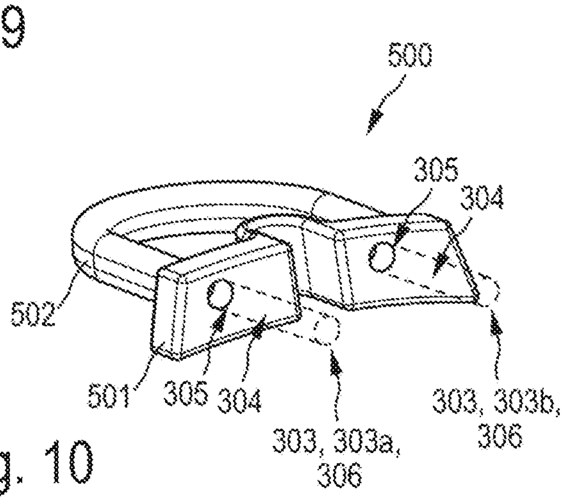
FIG. 10 shows a schematic perspective view, rotated relative to the view in FIG. 9, of the handle element from FIG. 9.
Figure 12:
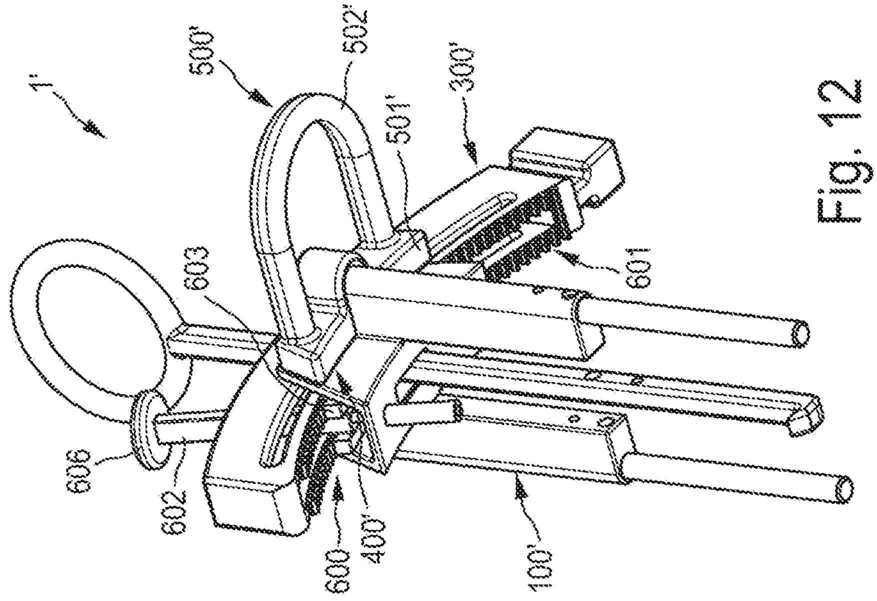
FIG. 12 shows a schematic perspective view, rotated relative to the view in FIG. 11, of the surgical instrument from FIG. 11.
Figure 11:
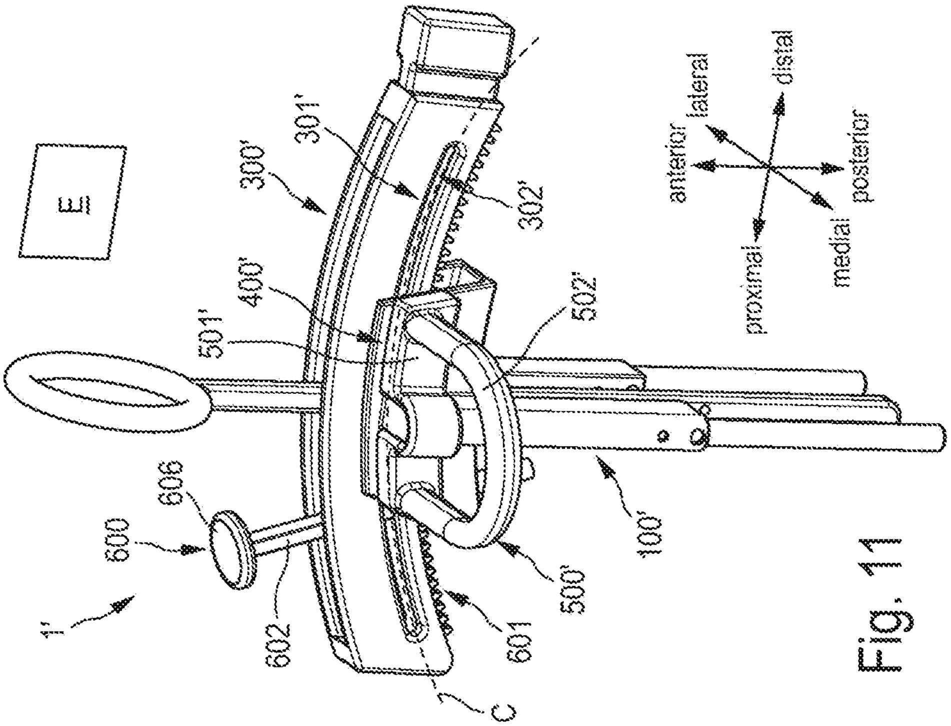
FIG. 11 shows a schematic perspective view of a further embodiment of the surgical instrument according to the present disclosure.
Figure 14:
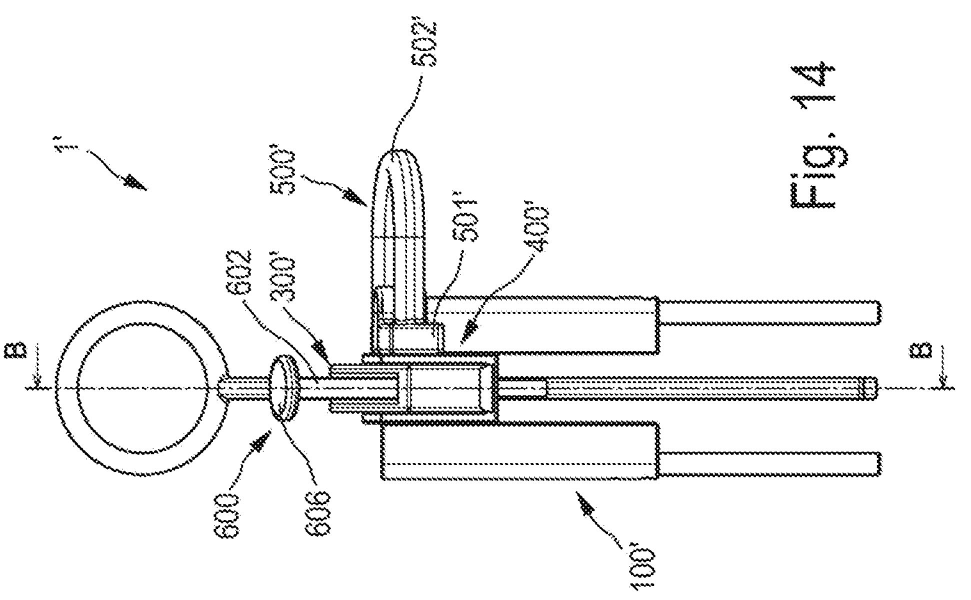
FIG. 14 shows a schematic front view of the surgical instrument from FIGS. 11 to 13.
Figure 13:
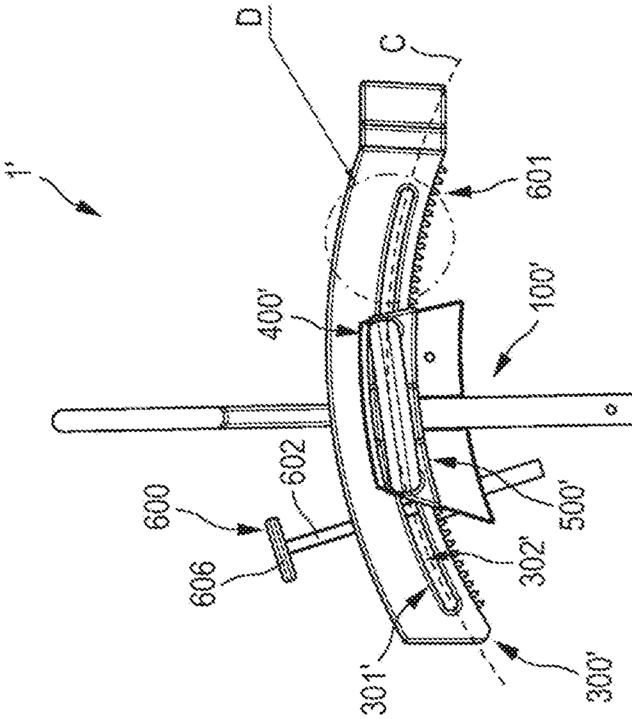
FIG. 13 shows a schematic side view of the surgical instrument from FIGS. 11 and 12.

FIG. 10 shows that the sliding members 303, **303*a*, 303*b* each have a sliding portion 304 and a push-fit portion 305. In the present case, the sliding members 303, 303*a*, 303*b* thus extend transversely to the guide track C between the sliding portion 304 and the push-fit portion 305. The same applies, mutatis mutandis, to the sliding members 303', 303*a*', 303*b*'. For slidingly movable guidance along the guide track C, the sliding portion 304 engages in the at least one guide slot 302, 302'. The push-fit portion 305 is releasably received in an associated receiving opening 401, 401' of the push-fit receiver 100, 100'. The push-fit portion 305 may be releasably received with tight fit in the associated receiving opening 401, 401'. The push-fit portion 305 may be received in the associated receiving opening 401, 401'** with an interference fit.

Figure 9:
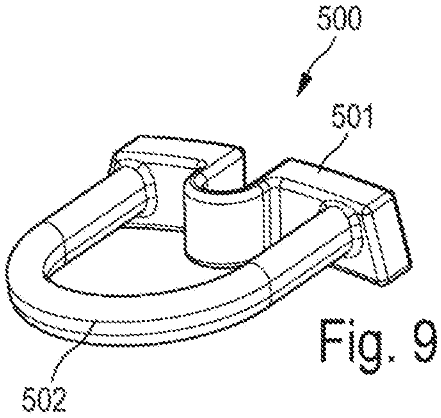
FIG. 9 shows a schematic perspective view of a carrier element of the surgical instrument from FIGS. 1 to 4.

The surgical instrument 1, 1' comprises a carrier element 500, 500', shown separately in FIGS. 9 and 10. The at least one sliding member 303, 303', 303*a*, 303*a*', 303*b*, 303*b*' is attached to the carrier element 500, 500'. In the present case, both sliding members 303, 303', 303*a*, 303*a*', 303*b*, 303*b*' are attached to the carrier element 500, 500'. The fastening of the at least one sliding member 303, 303', 303*a*, 303*a*', 303*b*, 303*b*' may be achieved by substance bonding and/or friction fit and/or form fit. For example, the at least one sliding member 303, 303', 303*a*, 303*a*', 303*b*, 303*b*' may be pressed into an associated bore of the carrier element 500, 500'. Alternatively, the carrier element 500, 500' and the at least one sliding member 303, 303', 303*a*, 303*a*', 303*b*, 303*b*' may be formed integrally with one another. In this case, the carrier element 500, 500' allows both sliding members 303, 303', 303*a*, 303*a*', 303*b*, 303*b*' to be removed simultaneously from the at least one guide slot 302, 302' and the associated push-fit receivers 101, 101'. Thus, the push-fit connection 400, 400' may be released with only one action. It is understood that, conversely, the carrier element 500, 500' may allow simultaneous mounting of both sliding members 303, 303', 303*a*, 303*a*', 303*b*, 303*b*' so as to form the push-fit connection 400, 400'. The carrier element 500, 500' comprises a base body 501, 501'. The carrier element 500, 500' also comprises a handle portion 502, 502' which protrudes from the base body 501, 501'. In the present case, the handle portion 502, 502' protrudes from the base body 501, 501' orthogonally to the guide track C. In this case, the handle portion 502, 502' is formed as a half ring. At least one human finger can be received in the half-ring handle portion 502, 502' for non-slip gripping of the handle portion 502, 502'. In the present case, the carrier element 500, 500' can be removed medially together with the attached sliding members 303, 303', 303*a*, 303*a*', 303*b*, 303*b*'. It is understood that mounting to form the push-fit connection 400, 400' takes place in the reverse direction, i.e. laterally.

In the embodiment of the surgical instrument 1 according to FIGS. 1 to 4, the sliding guide 301 comprises a hole row 308. The hole row 308 in this case is present on the at least one guide slot 302. The hole row 308 comprises several holes 307 extending transversely to the guide track C. The holes 307 serve for latching of the at least one sliding member 303, 303*a*, 303. In the present case, both sliding members 303, 303*a*, 303*b* may latch into the holes 307. In this case, the holes 307 extend longitudinally in the mediolateral direction. The holes 307 are spaced apart from one another along the guide track C. In this case, the holes 307 are equidistant from one another. The holes 307 establish several latching positions of the sliding members 303, 303*a*, 303*b*. The distance between the holes 307 relates to their extent axes. Thus, as in the present case, the holes 307 may be formed as radially intersecting bores. It is understood that, alternatively, the holes 307 may be configured as bores touching one another radially or tangentially, or as bores not touching one another. The guide slot 302 and, alternatively or additionally, the at least one sliding member 303, 303*a*, 303*b* is in this case spring-elastically deformable against a return force. The at least one sliding member 303, 303*a*, 303*b* is here held in its momentary latching position by means of the return force. Thus, to adjust the sliding member 303, 303*a*, 303*b* from its momentary latching position into a next latching position along the guide track C, the return force must be temporarily overcome.

In the embodiment according to FIGS. 11 to 16, the surgical instrument 1' has a fixing device 600. The fixing device 600 can be switched between a fixing state and a release state. The fixing state serves for fixing the first fastening device 100' relative to the guide device 300'. In the release state, this fixing is eliminated or released. This may be a form-fit and/or force-fit fixing. In the fixing state, the movability of the guide device 300' is fixed by means of the fixing device 600. The fixing device 600 comprises a tooth row 601 and an engagement device 602. The tooth row 601 extends parallel to the guide track C. The teeth and tooth gaps of the tooth row 601 are arranged alternately in a line parallel to the guide track. In the release state, the engagement device 602 is movable relative to the tooth row 601 parallel to the guide track C. The tooth row 601 is attached to the guide device 300'. The engagement device 602 is mounted on the first fastening device 100'. The engagement device 602 is mounted immovably transversely to the guide track C in at least one direction, in the present case both mediolaterally and proximodistally. The engagement device 602 in this case is mounted so as to be linearly movable in the anteroposterior direction. It is understood that conversely, alternatively, the engagement device 602 may be mounted on the guide device 303 and the tooth row 601 on the first fastening device 100', but this is not shown in the Figures. The engagement device 602 comprises a form-fit element 603. The form-fit element 603 is adjustable transversely to the guide track C between an engagement position and a release position in order to switch between the fixing state and the release state. In the engagement position, the form-fit element 603 engages in the tooth row 601. Conversely, in the release position, such an engagement is cancelled, i.e. released. The form-fit element 603 may be formed complementary to at least a part region of the tooth row 601. In this case, the form-fit element 602 has a toothing complementary to a part region of the tooth 601. According to FIGS. 11 to 21, two tooth rows 601 are arranged parallel to one another, each with an associated engagement device 602 with form-fit element 603.

Figure 15:
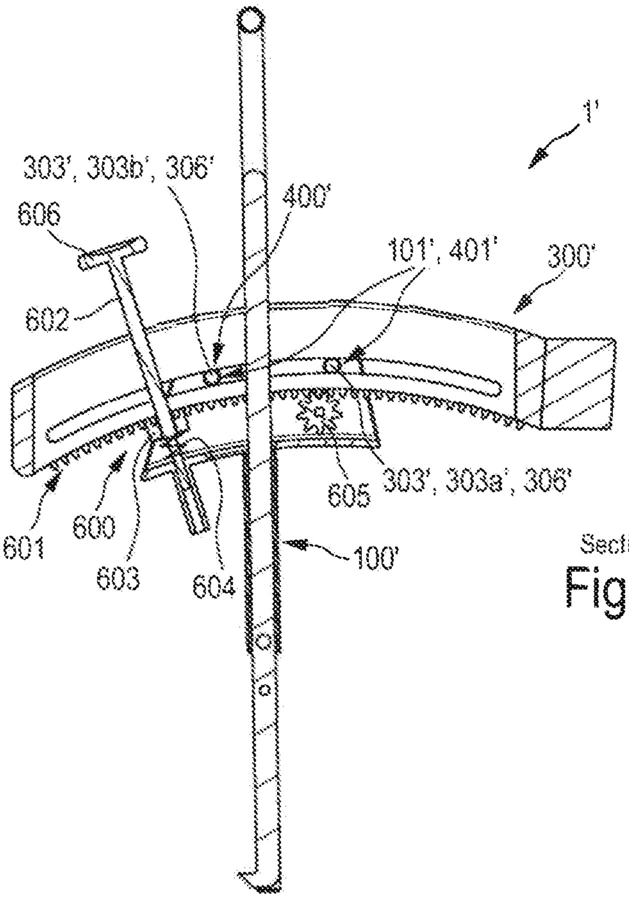
FIG. 15 shows a schematic sectional view along a section line B-B of the surgical instrument from FIGS. 11 to 14.
Figure 17:
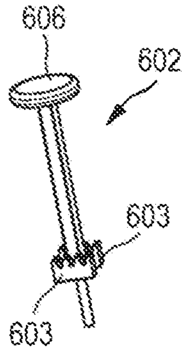
FIG. 17 shows a schematic perspective view of an engagement device of the surgical instrument from FIGS. 11 to 16.
Figure 16:
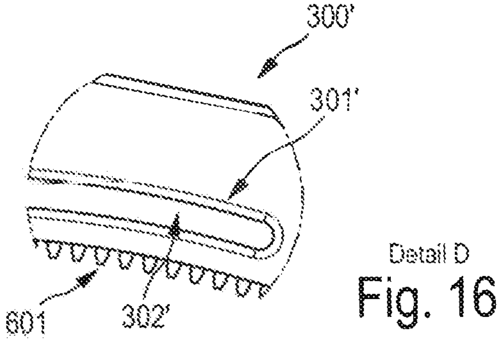
FIG. 16 shows a detail of the schematic side view in FIG. 13.
Figure 18:
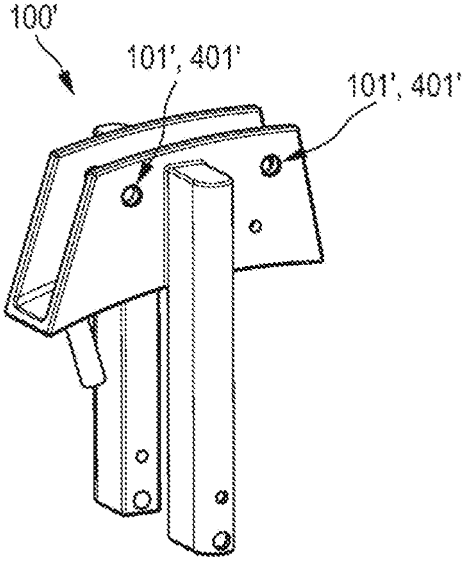
FIG. 18 shows a schematic perspective view of a first fastening device of the surgical instrument from FIGS. 11 to 16.
Figure 19:
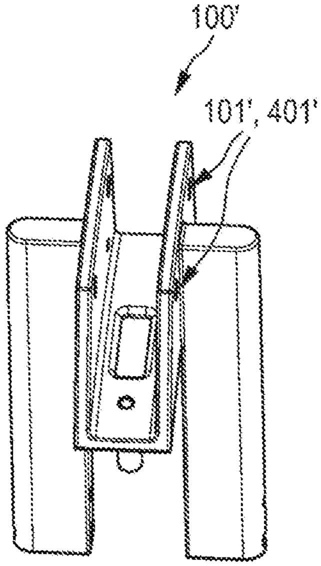
FIG. 19 shows a schematic perspective view, rotated relative to the view in FIG. 18, of the first fastening device from FIG. 18.
Figure 20:
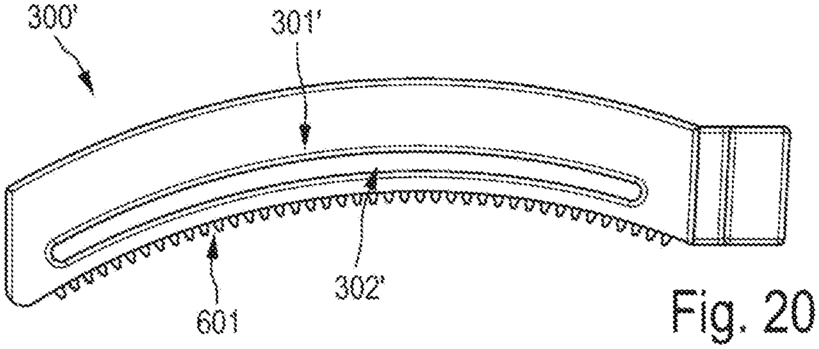
FIG. 20 shows a schematic side view of a guide device of the surgical instrument from FIGS. 11 to 16.
Figure 21:
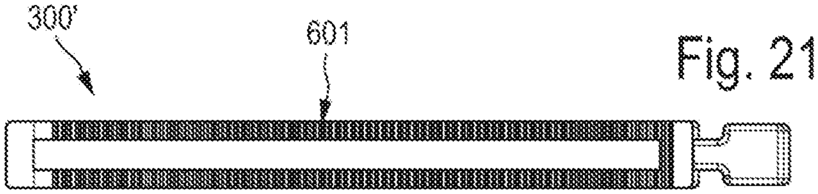
FIG. 21 shows a schematic underside view of the guide device from FIG. 20.

The engagement device 602 comprises a biasing member 604 for biasing the form fit element 603 into its engagement position, i.e. for generating a spring force, see FIG. 15. Thus, the spring force must be overcome in order to move the form-fit element 603 into the release position. As in this case, the engagement device 602 may comprise a gearwheel 605 which is mounted so as to be blockable and rotationally movable. The gearwheel 605 meshes with the tooth row 601. In the fixing state, the gearwheel 605 is blocked. Conversely, in the release state, the gearwheel 605 is rotationally movable relative to the tooth row 601. As an alternative or in addition to the blockable gearwheel 605, a non-blockable gearwheel (not shown in the Figures) may be provided which serves to support the relative guidance of the guide device 300' and the first fastening device 100'. In the present case, the engagement device 602 furthermore comprises an actuating element 606. By means of the actuating element 606, the engagement device 602 can be actuated—e.g. manually—for switching between the release state and the fixing state. In this case, the actuating element 606 is formed in the manner of a pushbutton. It is conceivable to equip the actuating element 606 with a "ballpoint pen mechanism". Such a mechanism prevents automatic return of the form-fit element 603 into its engagement position. It must be actuated a first time for adjustment into the release position and a second time for return to the engagement position, and vice versa.

The at least one sliding member 303, 303', 303*a*, 303*a'*, 303*b*, 303*b'* in this case is formed by a pin 306, 306'. In the present case, both sliding members 303, 303', 303*a*, 303*a'*, 303*b*, 303*b'* are formed by a respective pin 306, 306'. For example, the pin 306, 306' is cylindrical. The pin 306, 306' may be slotted and/or non-slotted on at least one of its axial ends. If, as in the present case, two pin-shaped sliding members 303, 303', 303*a*, 303*a'*, 303*b*, 303*b'* are provided, one of the pins 306, 306' may be slotted and one non-slotted. If the pin 306, 306' is slotted, an outer diameter of the slotted pin 306, 306' may be widened at the slotted axial end relative to the remaining region of the pin 306, 306'. Thus, an interference fit may be provided which holds the slotted pin 306, 306' in its mounting position on the guide device 300, 300' without hindering the movability of the guide device 300, 300'.

The surgical instrument 1 and the second fastening device 200 are part of the surgical instrument system 10. The surgical instrument system 10 may in addition comprise the femoral reference component and/or the tibial component.

The invention claimed is:

1. A surgical instrument for use in a total knee arthroplasty, the surgical instrument comprising:

a first fastening device having at least one receiver opening;

a guide device which is configured to be releasably coupled to the first fastening device, the guide device comprising at least one guide slot extending along a longitudinal direction wherein the at least one receiver opening extends in an orthogonal direction relative to the longitudinal direction when the guide device is coupled to the first fastening device; and at least one sliding member configured to be inserted along the orthogonal direction through the at least one receiver opening and into the at least one guide slot to thereby releasably connect the first fastening device with the guide device, wherein, when the first fastening device is connected with the guide device, the at least one sliding member is movable along the at least one guide slot in the longitudinal direction to thereby allow a relative movement guided in a sagittal guide plane between the first fastening device and the guide device;

wherein one of the first fastening device and the guide device is configured for releasable fastening to a femoral reference component, and the other of the first fastening device and the guide device is configured for releasable fastening to a tibial component.

2. The surgical instrument according to claim 1, wherein the at least one sliding member has a sliding portion and a push-fit portion, wherein, when the first fastening device is connected with the guide device, the sliding portion is located in the at least one guide slot and the push-fit portion is releasably received in the at least one receiver opening.

3. The surgical instrument according to claim 1, wherein the at least one sliding member comprises two sliding members that are spaced apart from one another, and the at least one receiver opening comprises two receiver openings, wherein each of the two sliding members is configured to be inserted along the orthogonal direction through a respective one of the two receiver openings and into the at least one guide slot.

4. The surgical instrument according to claim 1, further comprising a carrier element on which the at least one sliding member is fastened.

5. The surgical instrument according to claim 4, wherein the carrier element has a base body and a handle portion protruding from the base body.

6. The surgical instrument according to claim 5, wherein, when the first fastening device is connected with the guide device, the handle portion protrudes from the base body along the orthogonal direction.

7. The surgical instrument according to claim 1, further comprising a fixing device that is switchable between a fixing state for fixing relative movability between the first fastening device and the guide device, and a release state in which relative movability between the first fastening device and the guide device is not fixed.

8. The surgical instrument according to claim 1, wherein the at least one sliding member comprises a pin.

9. The surgical instrument according to claim 8, wherein the pin is cylindrical.

10. A surgical instrument for use in a total knee arthroplasty, the surgical instrument comprising:

a first fastening device having at least one receiver opening;

a guide device which is configured to be releasably coupled to the first fastening device, the guide device comprising at least one guide slot extending along a longitudinal direction wherein the at least one receiver opening extends in an orthogonal direction relative to the longitudinal direction when the guide device is coupled to the first fastening device; and at least one sliding member configured to be inserted along the orthogonal direction through the at least one receiver opening and into the at least one guide slot to thereby releasably connect the first fastening device with the guide device, wherein, when the first fastening device is connected with the guide device, the at least one sliding member is movable along the at least one guide slot in the longitudinal direction to thereby allow a relative movement guided in a sagittal guide plane between the first fastening device and the guide device, wherein the at least one guide slot comprises a hole row defined by holes extending through the guide device in the orthogonal direction for latching of the at least one sliding member, wherein the holes are spaced apart from one another along the longitudinal direction and establish several latching positions for the at least one sliding member.

11. A surgical instrument for use in a total knee arthroplasty, the surgical instrument comprising:

a first fastening device having at least one receiver opening;

a guide device which is configured to be releasably coupled to the first fastening device, the guide device comprising at least one guide slot extending along a longitudinal direction wherein the at least one receiver opening extends in an orthogonal direction relative to the longitudinal direction when the guide device is coupled to the first fastening device; and at least one sliding member configured to be inserted along the orthogonal direction through the at least one receiver opening and into the at least one guide slot to thereby releasably connect the first fastening device with the guide device, wherein, when the first fastening device is connected with the guide device, the at least one sliding member is movable along the at least one guide slot in the longitudinal direction to thereby allow a relative movement guided in a sagittal guide plane between the first fastening device and the guide device, wherein a portion of the guide device adjacent to the at least one guide slot and/or the at least one sliding member is spring-elastically deformable against a return force, wherein the at least one sliding member is held with the guide device by means of the return force.

12. A surgical instrument for use in a total knee arthroplasty, the surgical instrument comprising:

a first fastening device having at least one receiver opening;

a guide device which is configured to be releasably coupled to the first fastening device, the guide device comprising at least one guide slot extending along a longitudinal direction wherein the at least one receiver opening extends in an orthogonal direction relative to the longitudinal direction when the guide device is coupled to the first fastening device;

at least one sliding member configured to be inserted along the orthogonal direction through the at least one receiver opening and into the at least one guide slot to thereby releasably connect the first fastening device with the guide device, wherein, when the first fastening device is connected with the guide device, the at least one sliding member is movable along the at least one guide slot in the longitudinal direction to thereby allow a relative movement guided in a sagittal guide plane between the first fastening device and the guide device; and a fixing device that is switchable between a fixing state for fixing relative movability between the first fastening device and the guide device, and a release state in which relative movability between the first fastening device and the guide device is not, wherein the fixing device comprises a tooth row extending parallel to the at least one guide slot, and an engagement device which, in the release state, is adjustably movable relative to the tooth row parallel to the at least one guide slot, wherein the tooth row is fastened to the guide device and the engagement device is mounted on the first fastening device.

13. The surgical instrument according to claim 12, wherein the engagement device is mounted on the first fastening device immovably in at least one direction transversely to longitudinal direction.

14. The surgical instrument according to claim 12, wherein the engagement device comprises a form-fit element which is adjustably movable transversely to the at least one guide slot between an engagement position and a release position for switching between the fixing state and the release state, wherein the form-fit element engages in the tooth row in the engagement position, and the form-fit element disengages the tooth row in the release position.

15. The surgical instrument according to claim 14, wherein the engagement device comprises a biasing member which biases the form-fit element into the engagement position.

16. The surgical instrument according to claim 12, wherein the engagement device comprises a gearwheel which is mounted so as to be blockable and rotationally movable, and which meshes in the tooth row and blocks in the fixing state and is rotationally movable in the release state.

17. The surgical instrument according to claim 12, wherein the engagement device comprises an actuating element by which the engagement device is actuatable for switching between the release state and the fixing state.

18. The surgical instrument according to claim 17, wherein the engagement device is manually actuatable by the actuating element for switching between the release state and the fixing state.

19. A surgical instrument for use in a total knee arthroplasty, the surgical instrument comprising:

a first fastening device having at least one receiver opening;

a guide device which is configured to be releasably coupled to the first fastening device, the guide device comprising at least one guide slot extending along a longitudinal direction wherein the at least one receiver opening extends in an orthogonal direction relative to the longitudinal direction when the guide device is coupled to the first fastening device; and at least one sliding member configured to be inserted along the orthogonal direction through the at least one receiver opening and into the at least one guide slot to thereby releasably connect the first fastening device with the guide device, wherein, when the first fastening device is connected with the guide device, the at least one sliding member is movable along the at least one guide slot in the longitudinal direction to thereby allow a relative movement guided in a sagittal guide plane between the first fastening device and the guide device, wherein the at least one guide slot extends in arcuate form within the sagittal guide plane.

20. The surgical instrument according to claim 19, wherein one of the first fastening device and the guide device is configured for releasable fastening to a femoral reference component, and the other of the first fastening device and the guide device is configured for releasable fastening to a tibial component.

* * * * *